United States Patent [19]
Westermann

[11] Patent Number: 5,352,224
[45] Date of Patent: Oct. 4, 1994

[54] CORRECTION IMPLANT FOR THE HUMAN VERTEBRAL COLUMN

[75] Inventor: Kord Westermann, New York, N.Y.

[73] Assignee: Howmedica GmbH, Schoenkrichen, Fed. Rep. of Germany

[21] Appl. No.: 788,392

[22] Filed: Nov. 6, 1991

[30] Foreign Application Priority Data

Nov. 29, 1990 [DE] Fed. Rep. of Germany ... 9016227[U]

[51] Int. Cl.⁵ .............................................. A61B 17/56
[52] U.S. Cl. .................................... 606/61; 606/72; 606/73
[58] Field of Search ............... 606/61, 72, 73, 74, 606/75; 128/69; 623/17, 16; 411/372, 398, 400, 401

[56] References Cited

U.S. PATENT DOCUMENTS

| | | | |
|---|---|---|---|
| 4,289,123 | 9/1981 | Dunn | 606/61 |
| 4,653,481 | 3/1987 | Howland | 606/61 |
| 4,655,199 | 4/1987 | Steffee | 606/61 |
| 4,743,260 | 5/1988 | Burton | 606/61 |
| 4,913,134 | 4/1990 | Lugue | 606/61 |
| 5,067,955 | 11/1991 | Cotrel | 606/73 |
| 5,084,049 | 1/1992 | Asher | 606/61 |
| 5,092,867 | 3/1992 | Harms | 606/61 |
| 5,108,399 | 4/1992 | Eitenmuller | 606/73 |

Primary Examiner—Michael A. Brown
Attorney, Agent, or Firm—Peter C. Richardson; Lawrence C. Akers; Elizabeth O. Slade

[57] ABSTRACT

The invention provides a correction implant for the human vertebral column which is simply structured and consists of only a few parts. The correction implant according to the invention can be simply implanted and effectively fixes reset vertebra bodies in a selected position. The correction implant includes pedicle screws having slots for the accommodation of rods. The rods serve for the bracing of pairs of pedicle screws in a crosswise manner. The longitudinal connection between pedicle screws takes place by use of plate-shaped elongated elements having openings through which the pedicle screws are extended, with at least one opening being elongated so that the pedicle screws can be screwed in an accurate position.

11 Claims, 3 Drawing Sheets

CORRECTION IMPLANT FOR THE HUMAN VERTEBRAL COLUMN

BACKGROUND OF THE INVENTION

The German patent specification 26 49 042 discloses an implant for the human vertebral column including pedicle screws to be threaded into a verebra body and having an open-ended slot in the screw for the acccommodation of a compression rod. The compression rod is fixed to the screw head by nuts on the compression rod on both sides of the screw head. A pressure distribution plate is located below the screw head and is matched to the shape of the vertebra body. Frequently, the known implant is used pairwisely on both sides of the vertebra body, with the compression rod being adapted to the curvature of the vertebral column by bending it correspondingly. The stability of the compression rod is relatively low. A mutual bracing of the pairwisely located implants is not provided.

The German patent specification 32 19 575 discloses a correction implant for human vertebral columns using bone screws. The bone screws are connected with corner pieces interconnected in turn by a tension lock. By means of the tension lock, the distance between the bone screws can be varied. It is also known to tighten pairwisely arranged implants by tension wires. It is known that wires can be only loaded with tension and not with thrust or torsional forces. It is further disadvantageous with the known implant that the screws have to be actuated from different directions of access.

From the German patent specification 38 23 737, a correction and retaining means for the vertebral column is known, wherein pedicle screws are linked to support parts interconnected by a first and a second pair of threaded rods. The first pair of threaded rods interconnects the pedicle screws on one side of the vertebral column while the threaded rods of the second pair are crossing. The structure of the known correction implant is relatively expensive. The actuation of the screws takes place from different directions which means an additional difficulty for the surgeon.

SUMMARY OF THE INVENTION

The invention provides a correction implant for the human vertebral column which is simply structured and consists only of few parts. The correction implant according to the invention can be simply implanted and fixes effectively resetted vertebra bodies in any position thereof.

The known correction implant includes pedicle screws having slots for the accommodation of rods. The rods serve for the bracing of pairs of pedicle screws crosswisely. The longitudinal connection between pedicle screws takes place by plate-shaped elongated elements having openings through which the pedicle screws are extended, with at least one opening being elongated in order to screw the pedicle screws in a pedicle in an accurate position independent from its position relative to the elongated element. At the upper portion, the pedicle screws have a shoulder adapted to engage the facing surface of the associated plate-shaped element.

For the attachment to a pedicle screw, the rod may be provided with a thread so that two nuts may be screwed onto the rod from opposite sides of the pedicle screw to engage the head thereof. An embodiment of the invention, however, provides that the head of the pedicle screw has an outer thread onto which a nut may be threaded. The nut may engage the rod from above and fasten it in the slot, with the nut preventing the legs of the head forming the slot to be bent away from each other. Additionally or alternatively, the slot of the pedicle screw may have an inner thread into which a set screw may be threaded. In order to improve the attachment, the rod may be provided with grooves or a thread, respectively. According to a further embodiment of the invention, the rod may be out of round in cross section, preferably triangular, with the slot in the pedicle screw may be shaped correspondingly. By this, the rod is prevented from rotating in the head of the pedicle screw, and the rod may be loaded by considerable torsional forces. This improves the stabilizing effect of the implant of the invention.

According to another embodiment of the invention, the wall of the elongated hole of the plate-shaped elements has a plurality of arc-shaped pairwisely oppositely located recesses, and the shank of the pedicle screws below the shoulder and the recesses, respectively, are dimensioned such that a relative displacement of pedicle screw and elongated element is prevented when the shoulder engages the elongated element, however, is permitted when the shoulder has a distance from the elongated element. As already mentioned, the pedicle screw can be threaded into a pedicle at an arbitrary position relative to the elongated plate-shaped element. If the pedicle screw is tightened, the shoulder engages the plate, and plate and shoulder have a fixed relative position so that also the plate may be subject to forces for the fixation of the implant and the stabilization of the vertebra bodies.

The invention is to be described in more details along accompanied drawings.

DETAILED DESCRIPTION OF THE DRAWINGS

Figure 1:
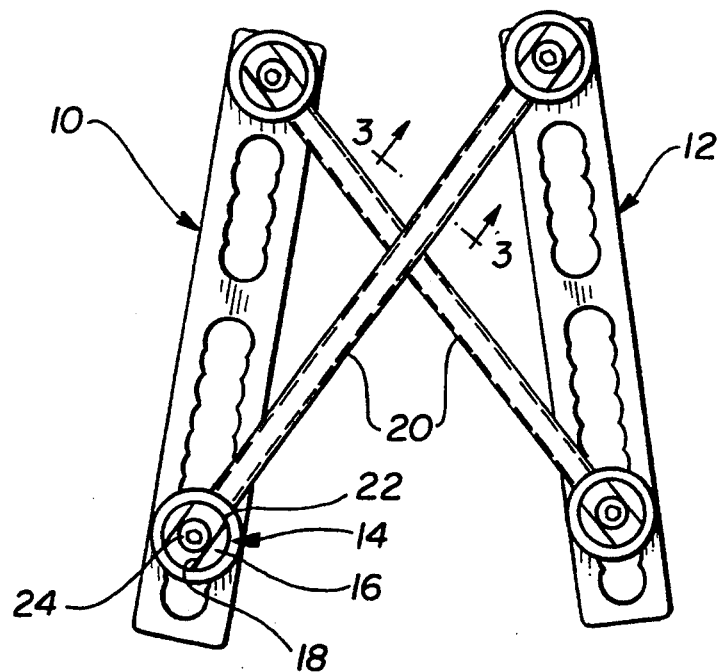
FIG. 1 is a plan view of a correction implant according to the invention.
Figure 1A:
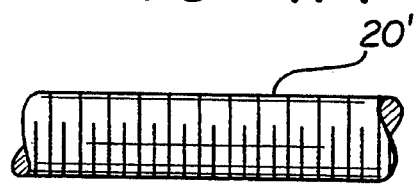
Figure 1B:
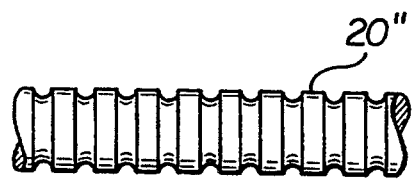
Figure 2:
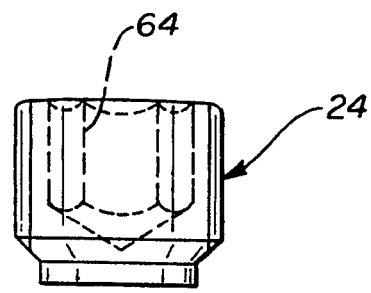
FIG. 2 is a side view of a set screw for the implant of FIG. 1 in an enlarged scale.

The correction implant shown in FIG. 1 includes two plate-shaped elements 10, 12. They cooperate with pedicle screws 14, only head 16 being visible in FIG. 1. The pedicle screws have a slot 18 for a threaded rod 20. In FIG. 2, four pedicle screws are crosswisely interlinked by threaded rods 20. A nut 22 is threaded onto head 16 of the pedicle screws 14. Therefore, head 16 has a corresponding outer thread. Slot 18 of the pedicle screws 14 has an inner thread into which a set screw 24 can be threaded. In the following, the parts are to be described which can be seen in FIG. 1 only partially.

Figure 3:
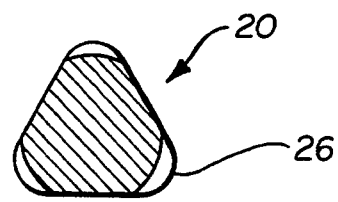
FIG. 3 is a cross-sectional view through a rod of the correction implant of FIG. 1 along line 3—3.

In FIG. 3, it can be seen that the rods 20 are triangular in cross section so that a thread 26 is only partially formed on peak areas. Notwithstanding, a nut can be threaded onto rod 20 if necessary.

Figure 4:
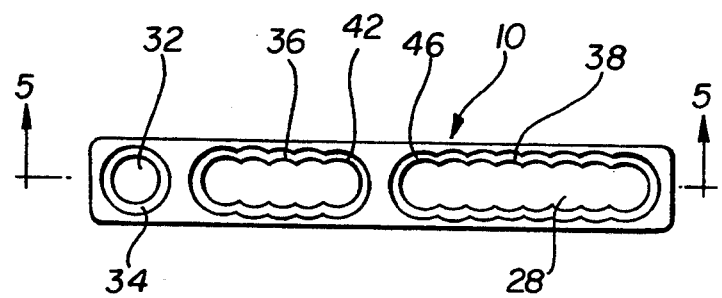
FIG. 4 is a plan view of a plate for the correction implant of FIG. 1.
Figure 5:
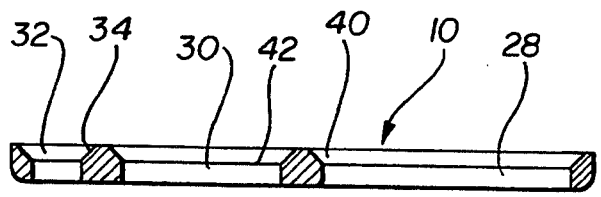
FIG. 5 is a cross-sectional view of the illustration of FIG. 4 along line 5—5.
Figure 6:
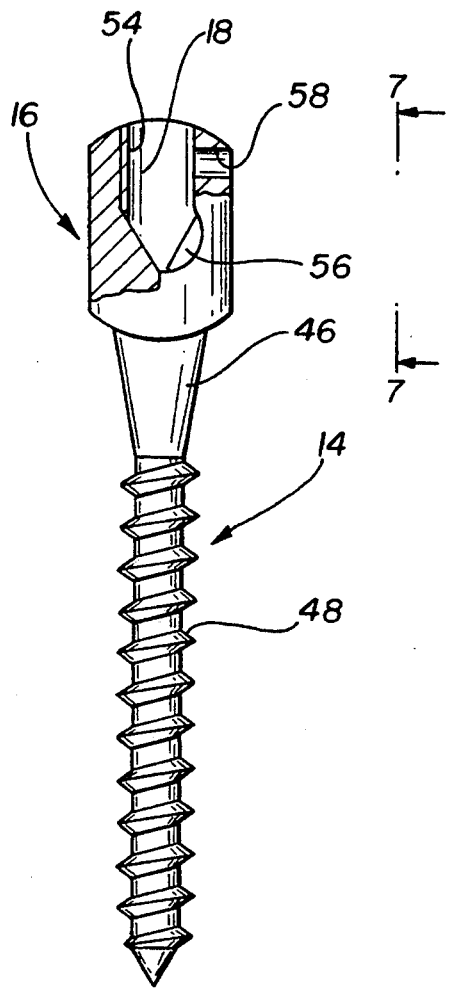
FIG. 6 is a side view of a pedicle screw of the implant of FIG. 1 in an enlarged scale.
Figure 7:
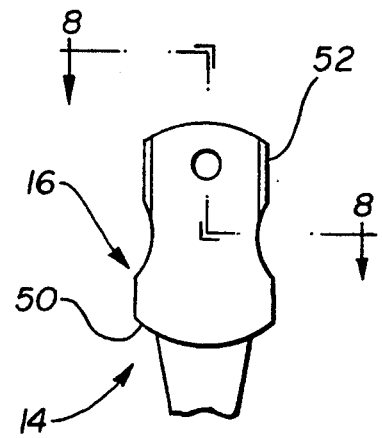
FIG. 7 is a side view of the head of the pedicle screw of FIG. 6 in direction 7.
Figure 8:
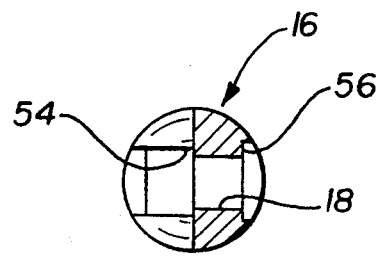
FIG. 8 is a cross-sectional view through FIG. 7 along line 8—8.

In FIGS. 4 and 5 it can be seen that plate 10 has two elongated holes 28, 30 and a circular hole 32. Circular hole 32 has a countersunk 34. The elongated holes 28, 30 have arc-shaped recesses 36, 38, respectively. A countersunk 40, 42 in the area of the recesses of the elongated holes 28, 30 is spherical.

The pedicle screw 14 has a head 16, a conical portion 46 joining to the head and a threaded shank portion 48 as well. The thread on shank portion 48 for example is a tapping thread.

The lower side of head 16 has a spherical shoulder 50. In the upper area, head 16 has an outer thread 52, and slot 18 has an inner thread 54 in the upper portion thereof. In the lower area, slot 18 is triangular in cross section and adapted to the cross-sectional contour of threaded rod 20. On two opposite sides of head 16, a countersunk 56 is provided. This countersunk for example serves for the accommodation of a nut threaded onto rod 20. A transverse bore 58 serves for the attachment of a tool (not shown) used to screw-in pedicle screw 14.

Figure 9:
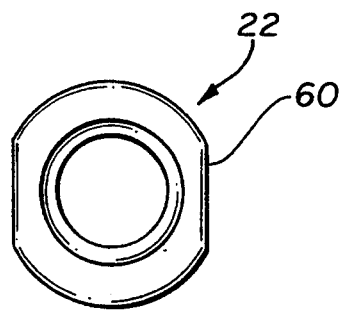
FIG. 9 is a plan view of a nut of the correction implant of FIG. 1.
Figure 10:
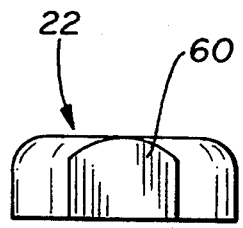
FIG. 10 is a side view of the nut of FIG. 9.

In FIGS. 9 and 10, a nut 22 can be seen which is to be threaded onto thread 52 of head 16 of pedicle screw 14. Nut 22 has flattened surface portions 60 on opposite sides for the engagement of a tool.

In order to implant the structure of FIG. 1 first, the pedicle screws 14 are threaded into the pedicle of vertebra bodies. The pedicle screws are extended through corresponding holes of plates 10, 12. Preferably, one pedicle screw is extended through circular hole 32 while the other is extended through one of the elongated holes 28, 30, respectively. Subsequently, the vertebra bodies are resetted by suitable means not shown. Thereafter, the pedicle screws are tightened and pressed into engagement with plates 10, 12 in order to fix the pedicle screws 14 relative to plates 10, 12. Then, rods 20 are inserted into slots 18 of pedicle screws 14 and fixed by means of set screws 24. As can be seen in FIG. 2, the set screws 24 have an outer thread which coacts with the inner thread of slot 18, with the set screws also having an inner hexagon 64. Finally, nut 22 is threaded onto the head of the pedicle screws which secures the set screw in the associated thread.

I claim:

1. Correction implant for the human vertebral column, comprising
    (a) four pedicle screws each having a threaded shank and a head having an underside and having an open-ended slot and a shoulder defined by said underside of said head and being adapted to be threaded into a vertebra,
    (b) a pair of rods arranged in mutually crossing relation, each rod of which is connected to heads of two pedicle screws and accommodated by said open-ended slots, each rod having a non-circular cross section and being fixable within said slots by fastening means, with each of said slots having a cross-section matched to said cross-section of one of said rods, and
    (c) a pair of elongated elements arranged substantially side-by-side and spaced apart from each other and also connected to two of said pedicle screws, each of said elongated elements being plate-shaped and having a plurality of openings, with said pedicle screws being extendable through said openings and at least one of said openings being elongated and having a plurality of arc-shaped oppositely located recesses, said threaded shank and said shoulder of each of said pedicle screws being dimensioned such that relative movement between each pedicle screw and said plate element is prevented if said shoulder engages said plate element, but is permitted if said shoulder is spaced apart a distance from said plate element.

2. Implant of claim 1, wherein said head of each of said pedicle screws has an outer thread onto which a nut may be threaded.

3. The implant of claim 1 wherein said slot of each pedicle screw head has an inner thread into which a set screw can be threaded.

4. The implant of claim 3, wherein each rod is grooved and is provided with a thread.

5. Implant of claim 1, wherein said slot adjacent to its bottom has a cross section matched to the cross section of said rod.

6. The implant of claim 5, wherein said rods and said slots are triangular in cross section.

7. The implant of claim 1, wherein a conical portion is provided between said thread of said pedicle screw and said shoulder.

8. Implant of claim 1, wherein said shoulder is spherical, and said holes in said plate-shaped elements have a countersunk facing said shoulder.

9. The implant of claim 8 wherein spherical countersunks are formed in the area of said recesses.

10. The implant of claim 1, wherein the walls of said elongated holes have a plurality of arc-shaped pairwisely oppositely located recesses, and said shank of said pedicle screws below said shoulder and said recesses, respectively, are dimensioned such that a relative movement of said pedicle screw and said plate element is prevented if said shoulder engages said plate element but is permitted if said shoulder is at a distance from said element.

11. An implant according to claim 1, wherein each of said elongated elements is plate-shaped and has a plurality of openings, with said pedicle screws being extendable through said openings, wherein at least one of said openings is elongated, and wherein at least one of said openings is of a shape which is substantially round.

* * * * *